US00PP22905P3

(12) United States Plant Patent
Doll

(10) Patent No.: US PP22,905 P3
(45) Date of Patent: Jul. 31, 2012

(54) ***HYDRANGEA* PLANT NAMED 'DOLGIP'**

(50) Latin Name: ***Hydrangea* hybrid**
Varietal Denomination: DOLGIP

(76) Inventor: Marie-France Doll, La Foret Fouesnant (FR)

( * ) Notice: Subject to any disclaimer, the term of this patent is extended or adjusted under 35 U.S.C. 154(b) by 0 days.

(21) Appl. No.: 12/928,140

(22) Filed: Dec. 2, 2010

(65) Prior Publication Data

US 2012/0144537 P1 Jun. 7, 2012

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Upov Plant Variety Dtabase 2011. Search for cultivar Dolgip. p. 1.*

* cited by examiner

*Primary Examiner* — Annette Para
(74) *Attorney, Agent, or Firm* — Cassandra Bright

(57) ABSTRACT

A new and distinct *Hydrangea* cultivar named 'DOLGIP' is disclosed, characterized by a very well branched, densely growing, floriferous plant. Flower longevity on the plant is very good, and over plant vigor moderate. The new variety is a *Hydrangea*, normally produced as an ornamental plant for containers or gardens.

1 Drawing Sheet

Latin name of the genus and species: *Hydrangea* hybrid.
Variety denomination: 'DOLGIP'.

BACKGROUND OF THE INVENTION

The new cultivar was discovered as a result of a planned breeding program directed by the inventor, Marie-France Doll a citizen of France. Seed was bulk collected in 2000 from unpatented, unnamed plants of *Hydrangea serrata* and *Hydrangea macrophylla* and subsequently planted. Due to the bulk seed collection, exact parents are unknown. The new variety was discovered as a seedling in 2003, by the inventor in a non commercial outdoor production area in La Foret Fouesnant, France.

Asexual reproduction of the new cultivar 'DOLGIP' by vegetative cuttings was first performed in 2003, at a research nursery in Angers, France. Multiple generations have since been produced and have shown that the unique features of this cultivar are stable and reproduced true to type in successive generations.

SUMMARY OF THE INVENTION

The cultivar 'DOLGIP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DOLGIP' These characteristics in combination distinguish 'DOLGIP' as a new and distinct *Hydrangea* cultivar:

1. Very well branched plant.
2. Densely growing plant habit.
3. Floriferous habit.

4. Long flower longevity on the plant.
5. Moderate vigor.

COMMERCIAL COMPARISON

'DOLGIP' can be compared to the commercial variety *Hydrangea macrophylla* 'Klaveren' unpatented. The two varieties are similar in many horticultural characteristics, including having a similar flower color. However, plants of 'DOLGIP' are denser, with more branches, and produce more flowers per plant. Additionally, 'DOLGIP' has darker foliage.

The new variety can also be compared to the commercial variety *Hydrangea macrophylla*, 'Love You Kiss', unpatented. *Hydrangea* 'DOLGIP' and *Hydrangea* 'Love You Kiss' are similar in most horticultural characteristics, however, plants of 'DOLGIP' are more vigorous, and produce more sterile flowers and branches per plant.

BRIEF DESCRIPTION OF THE PHOTOGRAPH

The accompanying photograph in FIG. 1 illustrates in full color a typical plant of 'DOLGIP" grown in a outdoors, in Angers, France, in a commercial 3 liter container.

Age of the plant photographed is approximately 2 years.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DOLGIP' plants grown outdoors, in Angers, France. The growing temperature ranged from approximately 10° C. to 35° C. daytime and 5° to 15° C. at night. Measurements and numerical values represent averages of typical plant types. Measurements were taken during the Fall.
Botanical classification: *Hydrangea* hybrid 'DOLGIP.'

PROPAGATION

Time to initiate roots: Approximately 3 weeks at approximately 20° C.
Root description: Fine, fibrous.
Root color: Near RHS White 155A.
Propagation method: Vegetative cuttings.

PLANT

Age of plant described: 24 months.
Growth habit: Flowering perennial shrub. Round, well branched.
Height: Approximately 80 cm.
Plant spread: Approximately 80 cm.
Growth rate: Moderate.
Branching characteristics: Very good free branching.
Length of lateral branches: Approximately 30 cm.
Number of lateral branches: Approximately 40.
Diameter of lateral branches: Approximately 1 cm.
Lateral branch shape: Round.
Lateral branch strength: Moderate.
Lateral branch color: Near RHS Yellow-Green 146B tinged with Greyed-Orange 174A.
Other stem or plant characteristics: Stems densely covered with lenticels.
*Lenticel length*.—Approximately 0.05 to 0.1 cm.
*Lenticel width*.—Approximately 0.05 cm.
*Lenticel color*.—Near RHS Greyed-Orange 174A.
Number of leaves per lateral branch: Approximately 12.
Age of plant described: 24 months Approximately.

FOLIAGE

Leaf:
*Arrangement*.—Opposite.
*Compound or single*.—Single.
*Average length*.—Approximately 11 cm.
*Average width*.—Approximately 7 to 8 cm.
*Shape of blade*.—Ovate.
*Apex*.—Acute.
*Base*.—Asymmetric.
*Attachment*.—Petiole attached to leaf lamina.
*Margin*.—Serrate, approximately 2 teeth per cm.
*Texture and appearance of top surface*.—Moderately glossy, non-pubescent.
*Texture and appearance of bottom surface*.—Matte, non-pubescent.
*Leaf internode length*.—Approximately 4 to 5 cm.
*Color*.—Young foliage upper side: Near RHS Yellow-Green 144 B. Young foliage under side: Near RHS Yellow-Green 146 C. Mature foliage upper side: Near RHS Yellow-Green 147A R.H.S. tinged with Greyed-Orange 166A. Mature foliage under side: Near RHS Yellow-Green 148B.
*Venation*.—Type: arcuate. Venation color upper side: Central vein near RHS Yellow-Green 154A. Lateral veins 145 D and 145C, both colors present individually. Venation color under side: Near RHS Yellow-Green 145 D and 145C, both colors present individually.
*Durability of foliage to stresses*.—Good resistance to physical stress.
Petiole:
*Average length*.—Approximately 1.5 cm.
*Diameter*.—Approximately 0.3 cm.
*Color*.—Near RHS Yellow-Green 145C, slightly tinged at the nodes with Greyed-Orange 174A.

FLOWER

Bloom period:
*Natural season*.—Continuous June through August.
Inflorescence:
*Arrangement*.—Single, sterile and fertile flowers arranged in terminal lacecap type panicles.
*Quantity of flowers per inflorescence*.—Fertile flowers, 200 approximately. Sterile Flowers, 15 to 20 approximately.
*Persistent or self-cleaning*.—Persistent.
*Fragrance*.—No.
Sterile flower:
*Diameter of entire flower*.—Approximately 4 cm.
*Depth of flower*.—Approximately 1 cm.
Petals:
*Length of petal*.—Approximately 2 cm.
*Width of petal*.—Approximately 1 cm.
*Apex*.—Obtuse.
*Shape of petal*.—Orbicular.
*Petal margin*.—Entire.
*Petal arrangement*.—Rotate, overlapping.
*Petal number*.—4 to 5.
*Petals fused*.—No.
*Petal texture*.—Smooth.
*Color*.—Upper surface at first opening: Near RHS Red-Purple 63C. Upper surface at maturity: Near RHS Red-Purple 63D. Upper surface at fading: Near RHS Red-Purple 65D. Under surface at first opening: Near RHS Red-Purple 63D. Under surface at maturity: Near RHS Red-Purple 63D. Under surface at fading: Near RHS Red-Purple 65D.
No Petaloids present.

OTHER CHARACTERISTICS

Disease resistance: Neither resistance nor susceptibility to diseases or pests has been observed in this variety.
Drought tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.
Fruit/seed production: No fruits/seeds detected to date.

What is claimed is:

1. A new and distinct cultivar of *Hydrangea* plant named 'DOLGIP' as herein illustrated and described.

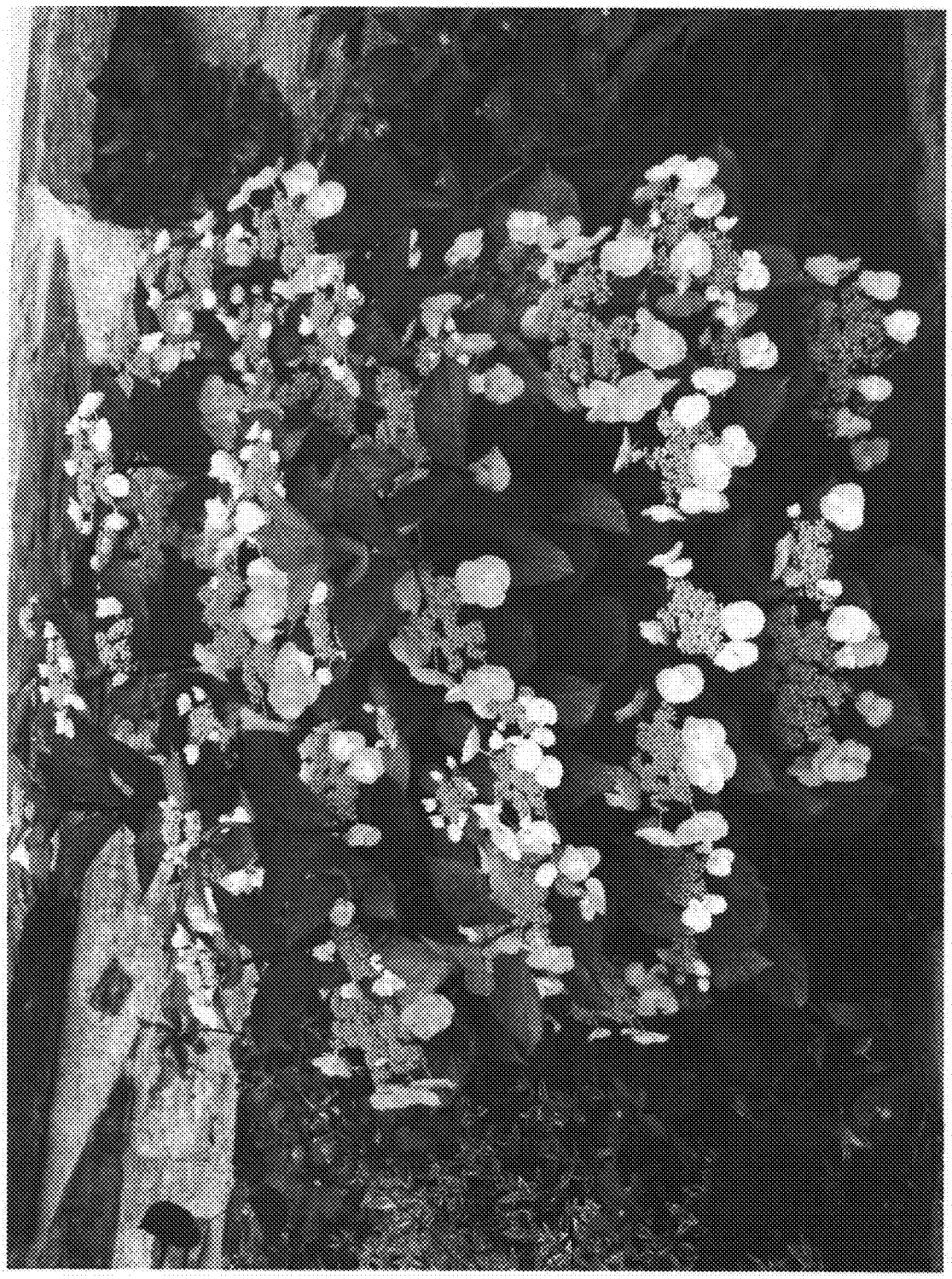

* * * * *